United States Patent [19]

Emheiser et al.

[11] Patent Number: 4,906,260
[45] Date of Patent: Mar. 6, 1990

[54] SELF-PRIMING INTRAVENOUS FILTER

[75] Inventors: William C. Emheiser, Chelsea; Robert Corbett, Manchester, both of Mich.

[73] Assignee: Gelman Sciences, Inc., Ann Arbor, Mich.

[21] Appl. No.: 336,509

[22] Filed: Apr. 12, 1989

Related U.S. Application Data

[63] Continuation of Ser. No. 080,757, Aug. 3, 1987, abandoned.

[51] Int. Cl.⁴ .............................................. B01D 46/00
[52] U.S. Cl. ................................. 55/159; 210/321.84; 210/436; 210/445; 210/446
[58] Field of Search ..................... 55/159; 210/321.84, 210/436, 445, 446

[56] References Cited

U.S. PATENT DOCUMENTS

| | | | |
|---|---|---|---|
| 2,530,283 | 11/1950 | Brown | 210/164 |
| 3,034,504 | 5/1962 | Winsor et al. | 128/214 |
| 3,149,758 | 9/1964 | Bush et al. | 222/189 |
| 3,506,130 | 4/1970 | Shaye | 210/436 |
| 3,523,408 | 8/1970 | Rosenberg | 55/159 |
| 3,803,810 | 4/1974 | Rosenberg | 55/159 |
| 3,854,907 | 12/1974 | Rising | 55/159 |
| 3,905,905 | 9/1975 | O'Leary et al. | 210/436 |
| 4,009,714 | 3/1977 | Hammer | 128/214 |
| 4,190,426 | 2/1980 | Ruschke | 55/185 |
| 4,238,207 | 12/1980 | Ruschke | 55/159 |
| 4,296,949 | 10/1981 | Muetterties et al. | 285/18 |
| 4,298,358 | 11/1981 | Ruschke | 55/185 |
| 4,340,479 | 7/1982 | Pall | 210/490 |
| 4,341,538 | 7/1982 | Vednay et al. | 55/159 |
| 4,525,182 | 6/1985 | Rising et al. | 55/159 |

Primary Examiner—Bernard Nozick
Attorney, Agent, or Firm—Arnold, White & Durkee

[57] ABSTRACT

This invention is directed to a membrane-type filter device. Vents located opposite the hydrophilic membrane remove entrapped gases in the inlet chamber of the housing. There are preferably two such vents on either end of the inlet chamber, of which the corners are preferably non-rectangular, and which remove entrapped gases from the fluid without regard to filter device orientation.

9 Claims, 3 Drawing Sheets

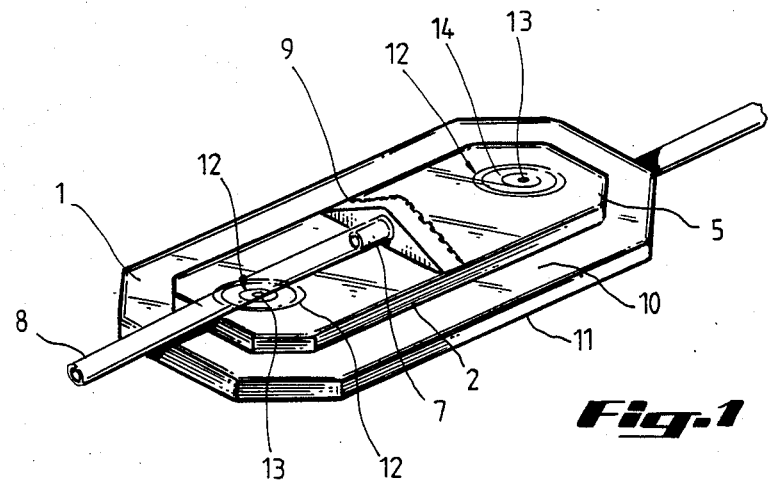
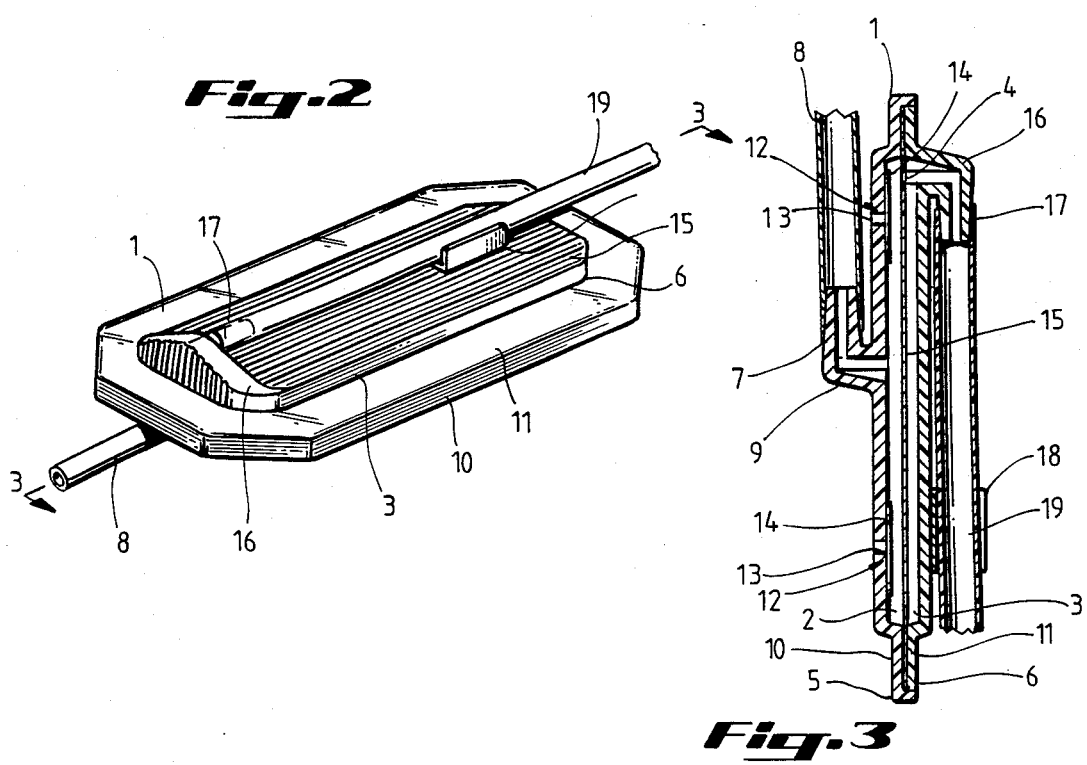

SELF-PRIMING INTRAVENOUS FILTER

This application is a continuation of application Ser. No. 080,757, filed Aug. 3, 1987, abandoned.

BACKGROUND OF THE INVENTION

A. Field of the Invention

This invention pertains to the field of membrane-type filter devices, particularly intravenous filter devices which employ both hydrophilic and hydrophobic membranes.

B. Description of Related Art

This invention relates broadly to membrane-type filter devices, and especially to filter devices used to remove impurities from liquids or fluids that are to be introduced intravenously to the human body. Some fluids useful with this invention include blood, plasma, glucose solutions and drugs. Other fluids useful with this invention are not listed but are well known to those having ordinary skill in the art.

One of the problems encountered with conventional membrane-type intravenous filter devices is the presence of gas. The fluid must be filtered before entering the patient in order to remove gas bubbles and contaminants. Gas in the housing or mixed with the liquid tends to prevent effective filtration of the liquid. When the filter is first attached to the patient and fluid flow is initiated, air frequently enters the lines or is already present in the filter device. This air tends to prevent the liquid from wetting a hydrophilic membrane which filters the liquid. A non-wetted hydrophilic membrane filter will generally not allow the liquid to pass. Thus, entrapped air tends to prevent fluid from entering the patient. It is therefore desirable to remove this entrapped air as quickly and continuously as possible.

Several devices are available to remove air from membrane-type filter devices. These devices make use of hydrophobic membranes which are capable of passing air but not liquids. Conventional intravenous filters employ this principle but have some shortcomings. For example, several commercial devices are not altogether satisfactory because they do not remove air through the outlet in the short time that is necessary. Some provide single vents; in these, air is sometimes entrapped in areas of the housing that are not contiguous to the hydrophobic membrane, especially when the orientation of the filter device makes it such that air cannot contact the hydrophobic membrane.

Various devices have attempted to correct these shortcomings. Some utilize rectangular filters to assist self-priming, with an inlet at the bottom and an outlet at the top of the filter. Such devices must be tilted from a horizontal plane in order to be self-priming. Some do not utilize a hydrophobic-type filter medium. Still other filter units employ a combination of hydrophilic and hydrophobic filters arranged side-by-side in alternate sequence. A disadvantage, however, is that this single plane configuration provides a hydrophobic zone on each end of the housing. Although these chambers appear to provide for the escape of entrapped air, they also create a zone where liquids can gather and be incapable of passing through either the hydrophilic membrane or the hydrophobic membrane. Further, drugs in intravenous fluids often have different densities than other fluids administered to the patient. When this is the case, the drugs may stratify and gather at these zones. Accordingly, if the filter unit is in a vertical position, the liquids will not immediately be administered to the patient. This could conceivably cause problems, especially if drugs must be administered quickly to the patient.

The problems enumerated in the foregoing are not intended to be exhaustive but rather are among many which tend to impair the effectiveness of previously known filter devices. Other noteworthy problems may also exist; however, those presented above should be sufficient to demonstrate that filter devices appearing in the art are not altogether satisfactory.

SUMMARY OF THE INVENTION

This invention is based on the discovery of a continuously venting, self-priming filter device. Although the filter device of the present invention may be used for filtering a wide variety of fluids, its main usefulness is for medical and diagnostic purposes, i.e., intravenous filter devices. This is because quick self-priming and continuous venting is particularly important for intravenous applications. A surprising advantage of this invention is that the shape of the first chamber, in conjunction with the location of vents close to each end of the chamber and opposite a hydrophilic membrane, assists the filter device in quickly purging air during priming and continuously venting gases entrapped in the chamber. Moreover, complete visibility of the hydrophilic membrane is possible through a transparent housing. These aspects of the invention provide continuous venting without a large hydrophobic membrane surface area.

In one aspect, the invention comprises a filter device comprising a housing having two spaced ends; a hydrophilic membrane extending between the ends dividing the housing into an inlet chamber and an outlet chamber; an inlet in the inlet chamber to direct fluid into the inlet chamber; a separate vent positioned sufficiently close to each end of the inlet chamber to contact gas at its respective said end of the inlet chamber, but without obstructing contact between the hydrophilic membrane and said respective end of the inlet chamber.

In another aspect, the invention comprises a filter device for an aqueous fluid, comprising a housing having two spaced ends; a hydrophilic membrane extending between the ends dividing the housing into an inlet chamber and an outlet chamber; an inlet in the inlet chamber to direct an aqueous fluid into the inlet chamber; a separate vent proximate each said end of the inlet chamber to vent gas from the inlet chamber; a hydrophobic membrane in each vent capable of transmitting gas in preference to water through the vent; each vent positioned sufficiently close to its respective said end of the inlet chamber to vent gas from said respective end but without obstructing contact between the hydrophilic membrane and said respective end.

In still another aspect, the invention comprises an intravenous filter device comprising a flat, substantially transparent housing and a hydrophilic membrane dividing the housing into two chambers, each chamber having an outer wall; an inlet to the housing for delivering fluid to the first chamber; an outlet to the housing for delivering fluid from the second chamber; and at least two vents in the wall of the inlet chamber opposite the surface of the hydrophilic membrane; the vents comprising a hydrophobic membrane attached to the inner wall of the first chamber; wherein the vents are compositely large enough to contact air bubbles throughout in the first chamber but small enough to provide visibility of the hydrophilic membrane through the housing.

In one embodiment, each vent of the invention is positioned in a plane spaced from the hydrophilic membrane.

In another embodiment the hydrophilic membrane extends around each vent.

In one embodiment the ratio of the surface area of the hydrophobic membrane to the surface area of the hydrophilic membrane is from about 1:20 to about 1:4.

In another embodiment, the first chamber is substantially rectangular; while in another the first chamber is octagonal; and in another, the first chamber is triangular.

In another embodiment, the vents are located from about 0.03 inches to about 0.10 inches from their respective end edges.

In still another embodiment, the second chamber has a plurality of ridges for supporting the hydrophilic membrane against a pressure differential across the hydrophilic membrane.

In yet another embodiment, the invention comprises a filter device wherein the inlet comprises a ridged distributor attached to the first chamber for delivering fluid to the first chamber.

And in another embodiment, the invention comprises a filter device wherein the outlet comprises a ridged distributor attached to the second chamber for delivering fluid from the second chamber.

BRIEF DESCRIPTION OF THE DRAWINGS

One preferred embodiment of the invention will be more fully described by the accompanying drawings wherein:

FIG. 1 is a perspective view of the outside surface of the inlet side of the preferred filter unit in accordance with the present invention.

FIG. 2 is a perspective view of the outside surface of the outlet side of the preferred filter unit in accordance with the present invention.

FIG. 3 is a cross-sectional view taken along line 1-1 of FIG. 1.

DETAILED DESCRIPTION OF AN EMBODIMENT OF THE INVENTION

The preferred embodiment of the invention is herein described in detail for enablement purposes. Referring to the drawings in FIGS. 1, 2 and 3 there is shown a new improved self-priming intravenous filter unit in accordance with the present invention. This particular unit which is the preferred embodiment comprises a substantially flat housing 1 which comprises an inlet or first chamber 2 and an outlet or second chamber 3 separated by a hydrophilic membrane 4. This housing 1 consists of an inlet housing half or portion 5 and an outlet housing half or portion 6. The filter unit is made by sealing the inlet housing portion 5 to the outlet housing portion 6 with the membrane 4 disposed therebetween.

The location of the hydrophilic membrane 4 between the two chambers 2, 3 is seen more easily in FIG. 3. As can be seen in FIG. 3, the two chambers are separated lengthwise by the hydrophilic membrane 4. Preferably, the housing 1 is transparent and the corners of the first or inlet chamber 2 are non-rectangular. An inlet to the housing delivers fluid to the first or inlet chamber 2. An outlet delivers fluid from the second or outlet chamber 3 after the fluid has passed through the membrane 4. The device also comprises vents 12 for releasing entrapped gas from the first chamber 2, wherein the vents 12 are positioned opposite the hydrophilic membrane 4. In general, a vent 12 must be positioned proximate each end of the first chamber 2 with sufficient hydrophobic membrane 14 adjacent the vent 12 to keep the vent accessible to gas in the first chamber 2. In one embodiment, the vent 12 includes an aperture 13 in the wall of the first chamber 12 and a hydrophobic membrane 14 attached between the aperture 13 and the interior of the first chamber 2.

The filter housing 1 is separated along one axis by a hydrophilic membrane 4. The housing 1 and membrane 4 thus define two chambers 5 and 6, each having a separate housing wall. The methods and essential materials for making the housing 1 are well known in the art and generally involve the use of clear synthetic resins. The overall size of the housing 1 is generally well known and is not substantially different from conventional intravenous filter devices. The preferred device, shown in FIGS. 1, 2, and 3, should have a void volume of from about 2.0 ml to about 4.0 ml, and preferably has a void volume of from about 2.8 ml to about 2.9 ml. Generally speaking, for intravenous applications, smaller filters are preferred over larger filters. A smaller filter is lighter and more convenient for the patient. Furthermore, the low void volume of a smaller filter means there is a smaller hold-up volume than with a larger filter; that is, there is less liquid remaining in the filter device at any given time. Low hold-up volume in intravenous filters is especially preferred for infants, who utilize low administration rates. Low void volume also helps the filter prime more quickly.

The filter housing 1 could also be constructed of flexible material such as polypropylene, polyethylene or polyvinyl chloride. However, because visibility is an important characteristic of this invention, the preferred embodiment is made from a substantially transparent material. A transparent filter provides visibility such that the fluid to be filtered can be readily seen by the patient, doctor or medical attendant. Thus, a gas bubble, foreign object or liquid contaminant blocking a portion of the hydrophilic membrane can be readily detected. Accordingly, a preferred material is an impact-modified acrylic such as acrylonitrile butadiene styrene terpolymer or any other plastic material that is durable, transparent and not unduly brittle. Materials such as polypropylene and polyethylene are less transparent and thus normally less preferred. However, a less transparent but more durable material may be preferred if high fluid pressures are to be employed.

The housing 1 of the present invention can be made by sealing two portions or halves of the housing 5 and 6 together to form a cavity. The housing portions 5, 6 are sealed by conventional techniques around the inlet flange 10 and the outlet flange 11. Any workable method of sealing the device against leakage is contemplated, including radio frequency weld sealing, hot melt sealing, ultrasonic sealing or solvent sealing. Although several methods of sealing are within the scope of the invention it has been found that radio frequency weldsealing is preferred for acrylic materials. In this embodiment, each housing half 5, 6 has a flange 10, 11 about its rim that fits to the flange of the other housing half. Before the two halves 5, 6 are sealed together, the hydrophilic membrane 4 is placed therebetween. The outer portions of the hydrophilic membrane 4 rest between the flanges 10, 11, and when the housing portions 5, 6 are sealed together, the hydrophilic membrane 4 is sealed in place, thus defining two chambers 2, 3. A tight seal is essential to prevent liquid in the housing 1 from leaking out or from passing through from the inlet or first chamber 2 to the outlet or second chamber 3 by any other way but through the hydrophilic membrane 4.

The hydrophilic membrane 4 of the present invention is of a type well known in the art. A preferred material for the membrane 4 is polysulfone, but the membrane 4 can also be made of a PVC acrylic copolymer, polyvialinadifluoride, cellulose, nylon or polyamide. The hydrophilic membrane 4 is microporous, and the mean pore size of the membrane is from about 0.1 micron to about 1.2 microns. The most preferred mean pore size is about 0.2 micron. The membrane 4 is shaped to fit the housing 1, being large enough for its edges to overlap onto the flanges 10, 11 so that, when sealed, the housing 1 is substantially leakproof. The membrane 4 surface area of the presently preferred embodiment is about 10 square centimeters. The preferred embodiment utilizes the smallest surface area possible so that a more economical unit can be produced at a reduced cost. For a unit having a hydrophilic membrane 4 surface area of about 10 square centimeters the unit has a preferred flow rate range of from about 15 ml to about 30 ml per minute at 1.5 psig. The operating fluid pressure range is from about 1 psig to about 45 psig.

Although the preferred housing 1 is flat, the shape is not critical. As illustrated in FIGS. 1 and 2, the corners of the inlet chamber 2 are preferably non-rectangular. Although in this embodiment, the corners are bevelled, they may also be rounded, depending on aesthetic preference, desired shape and economics in molding. Such non-rectangular corners reduce the tendency of gas bubbles to occupy the corners of the first or inlet chamber 2 and avoid the hydrophobic membranes 14 of the vents 12.

In this particular embodiment, the inlet chamber 2 is elongated octagon-shaped. The bevelled corners at each end of the chamber 2 direct air bubbles to exit through the vents 12. Although bevelled or rounded corners are part of the preferred embodiment, other shapes and corners are also part of the invention. For example, it is contemplated that a single sharp angle on either end, defining corners less than 90°, would also be operable and within the scope of the invention. For example, a first chamber 2 having the shape of a hexagon with two opposite sides shorter than the other four equal sides could, depending on the dimensions, provide the chamber with two opposing points, i.e., angles less than 90°. Such a first chamber must have vents located close enough to the opposite points to capture any air bubbles gathered there. One of the embodiments provides a triangular-shaped housing which is also within the scope of the invention. In that case, all the corners must necessarily be less than 90°. In that case, the vents are located sufficiently close to the corners so that air bubbles in that locale are effectively captured and released by the vents.

The inlet to the first chamber comprises an inlet connector or member 7 which may be connected to an inlet tubing 8. The inlet distributor 9 delivers fluid to the first chamber 2. In operation, liquid enters by a fluid source, such as a plastic tubing 8, which is attached to the inlet connector 7. From the inlet connector 7, the fluid enters the ridged distributor 9. In the preferred embodiment, this inlet connector 7 lies parallel to the housing 1 so that the interconnected tubing 8 can be conveniently taped to the arm of the patient. In the preferred embodiment, the inlet (comprised of the inlet connector 7 and the inlet distributor 9) is located approximately halfway between the two vents 12. This position, in conjunction with the multiple ridges in the inlet distributor 9, helps to provide an even distribution of liquid in the first or inlet chamber 2. Likewise, locating the inlet between the two vents 12 helps to keep the inlet connector 7 and fluid flow from obstructing the vents 12, which should be located at each end of the first or inlet chamber 2. The vents 12 are located on either side of the inlet. In the embodiment illustrated in FIGS. 1, 2 and 3, the aperture 13 is juxtaposed to the hydrophobic membrane 14, which is sealed to the inside surface of the first chamber 2. The preferred material for the hydrophobic membrane is polyester-supported PTFE manufactured by W.L. Gore & Associates, Elkton, Maryland. The preferred sealing method is ultrasonic welding.

The filter device also comprises an outlet for delivering fluid from the second chamber 3, usually to an outlet tubing 19 and from there to the patient. The outlet is comprised of the outlet distributor 16 and the outlet connector or member 17. The distributor 16 has ridges 15 to direct the existing liquid to the outlet connector 17 whereupon the liquid enters outlet tubing 19 to be administered intravenously to the patient. A flexible gripper 18 on the outside of the second chamber wall holds the outlet tubing 19 in place so that it will remain steady for intravenous administration of fluids to the patient. In the initial stages of operation, before the outlet tubing 19 is attached intravenously to the patient, the outlet generally passes air that has been purged from the housing 1. Once the filter device is primed, however, and the hydrophilic membrane 4 is wetted, fluid passes through the hydrophilic membrane 4 and exits through the outlet. The preferred embodiment provides a ridged outlet distributor 16 that receives liquid from the second or outlet chamber 3. This outlet distributor 16 channels the liquid into an outlet connector or member 17 to which may be attached the outlet tubing 19 which is attached intravenously to the patient.

A preferred embodiment of the present invention comprises a plurality of ridges 15 or other suitable supports in the second chamber 3 for supporting the hydrophilic membrane 4 against the pressure differential existing across the hydrophilic membrane 4 between the two chambers 2, 3. Such ridges 12 also help direct fluid toward the outlet distributor 16 and are well known in the art.

FIG. 3 shows the position of the vents 12 in relation to the hydrophilic membrane 4. The vents 12 are opposite the membrane 4 so that the liquid can contact the hydrophilic membrane 4 without interference from the vents 12. Generally, there should be enough space to prevent air in the inlet chamber from adhering to the inside wall and thus becoming immovably entrapped. The space should be small enough to have a low hold-up volume in the inlet chamber 2. Low hold-up volume, in conjunction with the shape of the inlet chamber 2 and the location of the vents 12, is believed to contribute to the quick self-priming and continuous venting of the device. As shown in this embodiment, the outlet should be on one end of the outlet chamber 3 to properly receive the filtered liquid and aid self-priming. If the outlet is not on the end, it is believed that the liquid will not exit in a satisfactory and efficient manner. In the embodiment shown in FIGS. 1, 2 and 3, the vents 12 comprise an aperture 13 in the wall of the inlet chamber. Between the inlet chamber 2 and the vent 12 is a sealed hydrophobic membrane 14 on the interior of the chamber 2. An important limitation for this embodiment is that the vents 12 be located on the wall of the inlet chamber 2 opposite the hydrophilic membrane 4. This ensures that liquid in the first chamber 2 is available for contact with the hydrophilic membrane 4 at all times and thus is available for filtering. In one embodiment, the external surface of the hydrophobic membrane 14 is juxtaposed to an aperture 13 in the wall of the inlet chamber 2 such that air flowing through the membrane 14 can escape quickly and immediately through the aperture 13 to the environment. The size of the aperture 13 is not particularly critical, except that it should be large enough to permit gas contacting the hydrophobic membrane 14 to escape to the environment. It should be small enough, however, to help keep the hydrophobic membrane 14 from possible damage. In a broader aspect, the invention is not limited to a single aperture for each vent. This is merely the preferred embodiment.

In a preferred embodiment, there are at least two vents 12, a vent located near or close to each end of an elongated octagon-shaped first or inlet chamber 2. The advantageous locations of these vents, i.e., close enough to the ends to receive entrapped gas, help contribute to self-priming and continuous ventilation. In another embodiment, a filter device could, however, have a single vent and still be within the scope of this invention. For example, the vent could constitute a strip of hydrophobic membrane material extending from one end of the wall of the first chamber to the other end of the wall. In effect, such a single vent would actually better be considered to be two end vents joined by an intermediate hydrophobic membrane.

Although close to the ends of the first chamber 2, preferably the vents 12 are not abutting the end edges. This provides room for the seal around the hydrophobic membrane. The location of the hydrophobic membrane 14,— i.e., the distance from the membrane to the end edges — should preferably be such that gas bubbles entrapped on either end of the first chamber 2 will touch a portion of the hydrophobic membranes 14, and thus escape through the apertures 13. In the specific embodiment illustrated in FIGS. 1, 2 and 3, a distance of between about 0.03 inch and 0.10 inch, measured when the membrane is dry, will be appropriate for bubbles of normal size.

Importantly, the hydrophobic membranes 14 are large enough such that at least one vent will almost always contact air bubbles in the first chamber 2. Additionally, the size of the hydrophobic membranes 14 should be reduced as much as possible to minimize cost, decrease possible damage, decrease possibility of vent leakage and provide a clear vision of the fluid being filtered. Indeed, this is one of the advantages offered by this invention. By following the invention, the vents 12 are small, unobtrusive, and yet effective for removing entrapped gases. In designing the filter device, aside from the visibility requirement, the ratio of hydrophobic membrane surface area to hydrophilic membrane surface area can be varied at will in order to achieve optimum results. The ratio of hydrophobic membrane surface area to hydrophilic surface area is generally from about 1:20 to about 1:4.

The double-vent aspect of the preferred embodiment is particularly advantageous in providing a substantially orientation-independent characteristic to the filter device in the removal of air bubbles. Especially when the inlet chamber 2 is elongated, it is contemplated that the device will be self-priming without regard to orientation. That is, regardless of the tilt of the device, gas bubbles, which generally rise, will be more likely to contact one of the hydrophobic membranes 14 and thus be released through the vents 12. Although there may be situations when the gas bubbles will not be directed to one side or the other, as when the filter device is perfectly horizontal, it is believed that the present device presents advantages not found in other devices of this type. It would even be possible to add a third vent somewhere between the first two vents to capture air bubbles not contiguous to the first two vents.

In operation, the preferred orientation of the elongated device is vertical, with one of the vents at the uppermost end and the other vent at the lower end. Thus, when fluid flows into the first chamber by way of the inlet, it tends to flow downward toward the first, lower vent, helping to drive out gas residing in the lower portion of the first chamber. As the fluid fills up the lower portion of the first chamber, it helps to push the air out through the second, upper vent. It also begins to flow through the hydrophilic membrane into the second or outlet chamber. Complete priming occurs only when air is no longer present in the housing and the hydrophilic membrane 4 is wetted by the fluid.

In operation, the fluid passes from the inlet chamber 2 through the hydrophilic membrane 4. After the fluid passes through the hydrophilic membrane 4 it runs down the grooves defined by the supporting ridges 15, which lead to the outlet. The ridged design of the inlet and outlet distributors 9, 17 are believed to increase the tolerance of the device to back pressure.

What is claimed is:

1. An intravenous filter device comprising:
   a flat, substantially transparent housing and a flat hydrophilic membrane dividing the housing into an inlet chamber and an outlet chamber, each chamber having an outer wall;
   an inlet to the housing for delivering fluid to the inlet chamber;
   an outlet to the housing for delivering fluid from the outlet chamber; and
   at least two vents in the outer wall of the inlet chamber opposite the surface of the hydrophilic membrane, said outer wall of said inlet chamber being parallel to said hydrophilic membrane, the vents comprising a hydrophobic membrane attached to the outer wall of the inlet chamber;
   wherein the vents are compositely large enough to contact air bubbles throughout in the inlet chamber but small enough to provide visibility of the hydrophilic membrane through the housing.

2. A filter, comprising a housing and a planar filter sheet of a hydrophilic filtering medium having a first surface and a second surface opposite said first surface wherein:
   said filter sheet is joined at its periphery to the interior of said housing, dividing the interior of said housing into an inlet chamber and an outlet chamber;
   said housing comprises an interior wall, and said interior wall of said housing opposite said first surface of said filter sheet is substantially parallel and coextensive with said filter sheet and has a first end and a second end with at least one aperture proximate said first end and opposite said filter sheet and with at least one aperture proximate said second end and opposite said filter sheet;

said apertures communicate with the exterior of said housing and have disposed between the exterior of said housing and said inlet chamber in said apertures a planar sheet of hydrophobic filtering medium, said housing wall opposite said first surface of said hydrophilic filter sheet having a first orifice intermediate said apertures for fluid communication between said inlet chamber and the exterior of said housing; and said first orifice communicates with exterior connection means, said housing wall opposite said second surface of said hydrophilic filter sheet having a second orifice for fluid communication between said outlet chamber and the exterior of said housing, said second orifice communicating with exterior connection means.

3. A filter as recited in claim 2 wherein the corners of the inlet chamber are bevelled.

4. A filter as recited in claim 2 wherein the ratio of the surface area of said planar sheet of hydrophobic filtering medium to the surface area of the filter sheet is from about 1:20 to about 1:4.

5. A filter as recited in claim 2 wherein said housing is substantially rectangular.

6. A filter as recited in claim 2 wherein:
said at least one aperture proximate said first end is located from about 0.03 inches to about 0.10 inches from said first end; and
said at least one aperture proximate said second end is located from about 0.03 inches to about 0.10 inches from said second end.

7. A filter as recited in claim 2 wherein said outlet chamber has a plurality of ridges for supporting said filter sheet against a pressure differential across said filter sheet.

8. A filter as recited in claim 2 wherein said first orifice comprises a ridged distributor for delivering fluid from a point exterior said housing to said inlet chamber.

9. A filter as recited in claim 2 wherein said second orifice comprises a ridged distributor attached to the outlet chamber for delivering fluid from said outlet chamber to a point exterior to said housing.

* * * * *